United States Patent
Holm et al.

(10) Patent No.: US 9,452,087 B2
(45) Date of Patent: Sep. 27, 2016

(54) WOUND DRESSING ASSEMBLY

(75) Inventors: David R. Holm, Hudson, WI (US); Kevin G. Lundquist, Hudson, WI (US); Richard L. Jacobson, Stillwater, MN (US)

(73) Assignee: 3M INNOVATIVE PROPERTIES COMPANY, Saint Paul, MN (US)

( * ) Notice: Subject to any disclaimer, the term of this patent is extended or adjusted under 35 U.S.C. 154(b) by 0 days.

(21) Appl. No.: 14/131,568

(22) PCT Filed: Jul. 10, 2012

(86) PCT No.: PCT/US2012/046001
§ 371 (c)(1),
(2), (4) Date: Mar. 14, 2014

(87) PCT Pub. No.: WO2013/009725
PCT Pub. Date: Jan. 17, 2013

(65) Prior Publication Data
US 2014/0378923 A1 Dec. 25, 2014

Related U.S. Application Data

(60) Provisional application No. 61/506,828, filed on Jul. 12, 2011.

(51) Int. Cl.
*A61F 13/00* (2006.01)
*A61F 13/02* (2006.01)
(Continued)

(52) U.S. Cl.
CPC ..... *A61F 13/0206* (2013.01); *A61F 13/00085* (2013.01); *A61F 13/0266* (2013.01); *A61L 15/24* (2013.01); *A61L 15/58* (2013.01); *A61F 2013/00817* (2013.01)

(58) Field of Classification Search
CPC ................. A61F 2013/00119; A61F 13/0206; A61F 13/0213; A61F 13/022; A61F 2013/00225; A61F 2013/00702; A61F 2013/00778; A61F 2013/00782; A61F 2013/0074; A61F 2013/00744; A61F 2013/00855; A61F 2013/00097; A61F 2013/00404; A61F 2013/00761; A61F 2013/00523; A61F 2013/00548; A61F 2013/00604; A61F 2013/00608; A61F 13/0283; A61F 2013/00229; A61F 2013/00719; A61F 2013/00723; A61F 2013/0077; A61F 2013/00774; A61F 2013/5113; A61F 2013/51134; A61F 2013/530802; A61F 13/0226; A61F 2013/53463; A61F 13/00085; A61F 2013/00817; A61F 13/0269; A61F 2013/00302; A61F 2013/00553; A61F 2013/00561; A61F 2013/00565; A61F 2013/795; A61F 15/00; A61F 13/023; A61F 13/0246; A61F 13/0279
USPC ........... 442/22, 26; 602/41, 46, 58; 427/2.31
See application file for complete search history.

(56) References Cited

U.S. PATENT DOCUMENTS

RE24,906 E 12/1960 Ulrich
3,389,827 A 6/1968 Abere
(Continued)

FOREIGN PATENT DOCUMENTS

CN 2287943 Y 8/1998
CN 2681756 Y 3/2005
(Continued)

OTHER PUBLICATIONS

International Search Report for PCT International Application No. PCT/US2012/046001 Mailed on Oct. 31, 2012, 3 pages.

*Primary Examiner* — Peter S Vasat
(74) *Attorney, Agent, or Firm* — 3M Innovative Properties Company; Lynn R. Hunsberger (57) ABSTRACT

The disclosed wound dressing assembly includes an absorbent body with removeably attached tape strips partially secured to the absorbent body for a simple and efficient way to provide for securement of an absorbent body while also making tape strips readily available for additional securement needs. The wound dressing assembly comprises an absorbent body comprising a first skin-facing surface and a second surface, opposite the first surface, a first tape strip comprising a substrate coated with a soft, elastomeric adhesive, wherein a first portion of the first tape strip is removeably secured to the absorbent body, and wherein a second portion of the first tape strip is removably secured to a tape release layer to form a tab.

7 Claims, 3 Drawing Sheets

(51) Int. Cl.
*A61L 15/24* (2006.01)
*A61L 15/58* (2006.01)

(56) References Cited

U.S. PATENT DOCUMENTS

| | | | |
|---|---|---|---|
| 4,094,316 A | 6/1978 | Nathanson | |
| 4,112,213 A | 9/1978 | Waldman | |
| 4,161,176 A * | 7/1979 | Harris et al. | 602/58 |
| 4,310,509 A | 1/1982 | Berglund | |
| 4,323,557 A | 4/1982 | Rosso | |
| 4,472,480 A | 9/1984 | Olson | |
| 4,595,001 A | 6/1986 | Potter | |
| 4,737,410 A | 4/1988 | Kantner | |
| 4,753,232 A | 6/1988 | Ward | |
| 4,773,408 A * | 9/1988 | Cilento et al. | 602/49 |
| 5,160,315 A | 11/1992 | Heinecke | |
| 5,415,627 A * | 5/1995 | Rasmussen et al. | 602/57 |
| 5,520,629 A * | 5/1996 | Heinecke et al. | 602/57 |
| 5,931,800 A | 8/1999 | Rasmussen | |
| 6,262,330 B1 * | 7/2001 | Fujisawa et al. | 602/54 |
| 6,479,724 B1 | 11/2002 | Areskoug | |
| 493,230 A1 | 7/2004 | Liedtke | |
| 6,838,589 B2 | 1/2005 | Liedtke | |
| 511,005 A1 | 10/2005 | Liedtke | |
| 7,030,288 B2 | 4/2006 | Liedtke | |
| 7,612,248 B2 | 11/2009 | Burton | |
| 2004/0162512 A1 | 8/2004 | Liedtke | |
| 2008/0233348 A1 | 9/2008 | Ishiwatari | |

FOREIGN PATENT DOCUMENTS

| | | |
|---|---|---|
| CN | 1756519 | 4/2006 |
| CN | 201308582 Y | 9/2009 |
| DE | 10 2005 00514 | 8/2006 |
| EP | 2796119 A1 * | 10/2014 |
| WO | WO 92-11333 | 7/1992 |
| WO | WO 94/13237 | 6/1994 |
| WO | WO 96-14094 | 5/1996 |
| WO | WO 2010-056541 | 5/2010 |
| WO | WO 2010-056543 | 5/2010 |

* cited by examiner

WOUND DRESSING ASSEMBLY

CROSS REFERENCE TO RELATED APPLICATIONS

This application is a national stage filing under 35 U.S.C. 371 of PCT/US2012/046001, filed Jul. 10, 2012, which claims priority to U.S. Provisional Application No. 61/506,828, filed Jul. 12, 2011, the disclosures of which are incorporated by reference in their entirety herein.

FIELD

The present disclosure relates to a wound dressing assembly. In particular, the present disclosure relates to a wound dressing assembly comprising an absorbent body with removably attached tape strips partially secured to the absorbent body.

BACKGROUND

Absorbent wound dressings are often used on wounds with moderate to high drainage of wound fluid where typically the patient's skin at the wound and periwound area is very fragile. An absorbent wound dressing includes an absorbent material, such as foam, for placement adjacent to the wound. The absorbent material often has a film covering the backside to prevent passage of wound fluid entirely through the absorbent material.

Absorbent wound dressings are often used with an overlying wrap bandage, such as with a 3M Coban™ Compression Bandage, available from 3M Company, St. Paul Minn. When applying the absorbent wound dressing to the patient, it is helpful to have an ability to hold the absorbent wound dressing in place until the overlying bandage is wrapped around the absorbent wound dressing and more securely holds the absorbent wound dressing.

To help with holding of the absorbent wound dressing, an adhesive may be included on the skin-facing surface of the absorbent material. However, the adhesive can limit the ability of the absorbent material to easily absorb wound exudates. Also, it may be undesirable to include adhesive on the skin-facing surface because of the sensitive and fragile skin of the patient.

An overlying thin-film dressing, such as a 3M Tegaderm™ Dressing available from 3M Company of St. Paul, Minn., can be applied over an absorbent wound dressings to secure the absorbent wound dressing to the patient. Similarly, dressings that include the overlying thin-film backing with an absorbent core, such as a 3M Tegaderm™ HP Foam Dressing available from 3M Company of St. Paul, Minn. can be used on high exudating wounds. These products work well, but there may be instances where it would be desirable to not have an adhesive in contact with fragile skin for an extended period of time.

Tape can be used to secure the absorbent wound dressing to the patient. However, it can be cumbersome to pull a tape section from a roll of tape while trying to secure the wound dressing to the patient. Also, many tapes have too high of a peel strength and either may damage the fragile skin upon removal or may adhere to strongly to the back side of the absorbent wound dressing, which prevents the tape from being removed prior to application of the overlying wrap bandage.

SUMMARY

The disclosed wound dressing assembly includes an absorbent body with removably attached tape strips partially secured to the absorbent body. The removably and partially secured tape strips are repositionable and provide a simple and efficient way to provide for securement of an absorbent body while also making tape strips readily available for additional securement needs, such as securement of medical devices or tubing.

In one embodiment, the wound dressing assembly comprises an absorbent body comprising a first skin-facing surface and a second surface, opposite the first surface, a first tape strip comprising a substrate coated with a soft, elastomeric adhesive, wherein a first portion of the first tape strip is removably secured to the absorbent body, and wherein a second portion of the first tape strip is removably secured to a tape release layer to form a tab. In one embodiment, the first portion of the tape strip is removably secured to the second surface of the absorbent core. In one embodiment, the second portion of the tape strip extends beyond a perimeter of the absorbent body. In one embodiment, the adhesive on the tape strip is a silicone adhesive. In one embodiment, the absorbent body comprises an absorbent core and a film backing. In one embodiment, the film backing extends beyond the perimeter of the absorbent core. In one embodiment, the absorbent body comprises an absorbent core contained within a pouch. In one embodiment, the absorbent core comprises a foam, nonwoven, woven, knitted, superabsorbent or combinations of one or more thereof. In one embodiment, the wound dressing further comprises a skin-contact adhesive on the skin-facing surface of the absorbent body. In one embodiment the wound dressing further comprises a second release liner covering at least the skin-facing surface of the absorbent body. In one embodiment, the wound dressing further comprises a second tape strip comprising a substrate coated with a soft, elastomeric adhesive, wherein a first portion of the second tape strip is removably secured to the absorbent body and a second portion of the second tape strip is removably secured to a second tape release layer to form a tab.

In one embodiment, the wound dressing assembly comprises an absorbent body comprising a first skin-facing surface and a second surface, opposite the first surface and a perimeter, a first tape strip comprising a substrate coated with a soft, elastomeric adhesive, wherein a first portion of the first tape strip is removably secured to the absorbent body and a second portion of the first tape strip is removably secured to a first tape release layer and extends beyond the perimeter of the absorbent body to form a first tab, a second tape strip comprising a substrate coated with a soft, elastomeric adhesive, wherein a first portion of the second tape strip is removably secured to the absorbent body and a second portion of the second tape strip is removably secured to a second tape release layer and extends beyond the perimeter of the absorbent body to form a second tab, wherein a portion of the first tape release layer covers at least a portion of the first skin-facing surface of the absorbent body and a portion of the second tape release layer covers at least a portion of the first skin-facing surface of the absorbent body.

In one embodiment, the tape strips may be removed from the absorbent body without damaging, distorting, or tearing any portion of the absorbent body, including any backing, if included. The removed tape strips can then be used to secure the absorbent body to skin or to secure other medical components such as tubing.

While the above-identified drawings and figures set forth embodiments of the invention, other embodiments are also contemplated, as noted in the discussion. In all cases, this disclosure presents the invention by way of representation and not limitation. It should be understood that numerous other modifications and embodiments can be devised by those skilled in the art, which fall within the scope and spirit of this invention.

The figures may not be drawn to scale.

DETAILED DESCRIPTION

Figure 1:
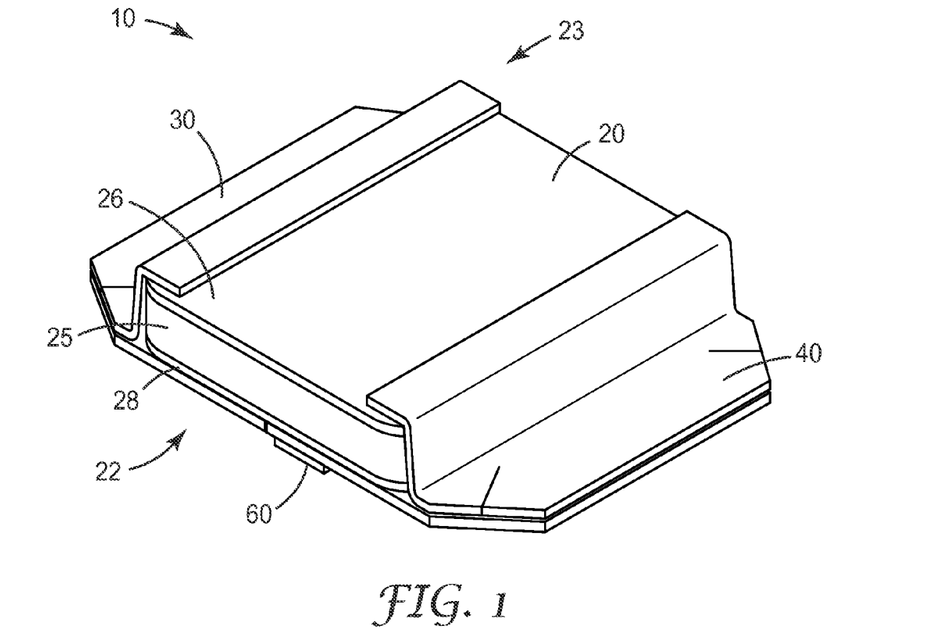
FIG. 1 is a perspective view of an embodiment of a wound dressing assembly.
Figure 2:
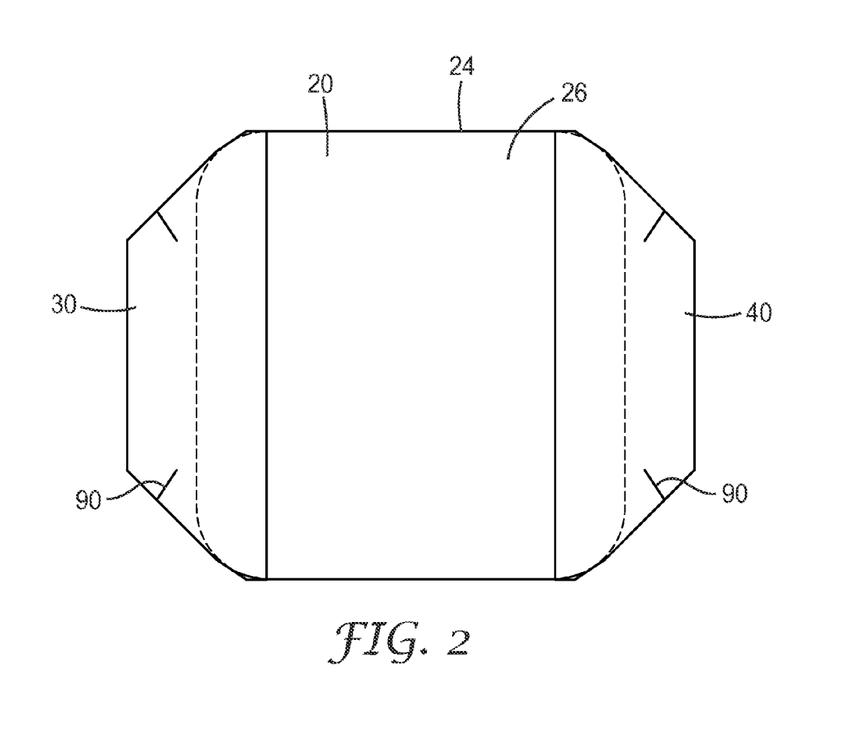
FIG. 2 is a top view of the embodiment of FIG. 1.
Figure 3:
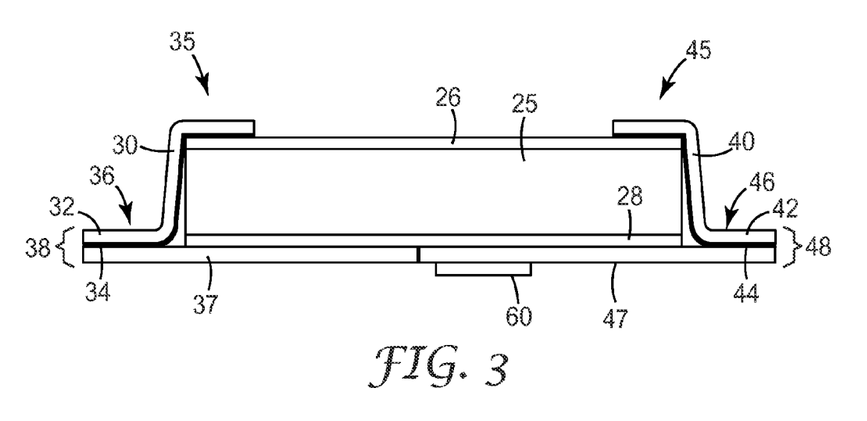
FIG. 3 is a side view of the embodiment of FIG. 1.
Figure 4:
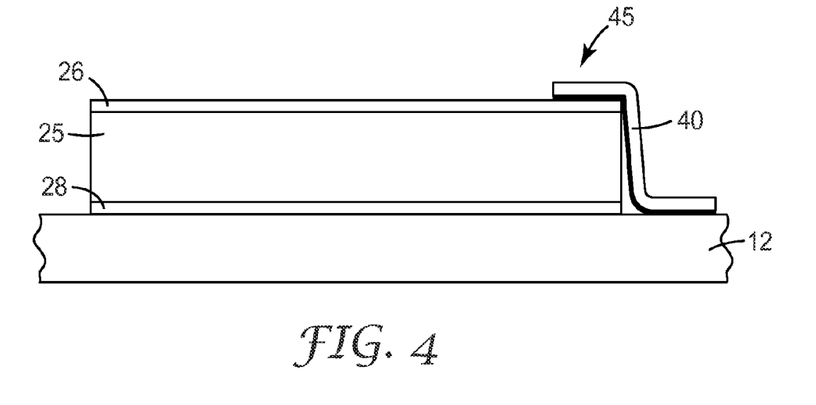
FIG. 4 is a side view of the embodiment of FIG. 1 applied to skin with a first tape strip removed.

FIG. 1 is a perspective view of an embodiment of a wound dressing assembly 10. FIG. 2 is a top view of the wound dressing assembly 10 shown in FIG. 1. FIG. 3 is a side view of the wound dressing assembly 10 shown in FIG. 1. FIG. 4 is a side view of the wound dressing assembly 10 shown in FIG. 1 applied to skin 12 with a first tape strip 30 removed.

The wound dressing assembly 10 comprises an absorbent body 20 and a first tape strip 30. In the embodiment shown in FIGS. 1-4, the wound dressing assembly 10 further comprises a second tape strip 40.

The absorbent body 20 includes a first skin-facing surface 22 and a second surface 23, opposite the skin-facing surface surrounded by a perimeter 24. The absorbent body 20 includes an absorbent core 25 that is able to absorb wound fluid and retain some or a majority of the absorbed wound fluid. The absorbent core 25 can be any material able to absorb wound fluid and retain some or a majority of the absorbed wound fluid.

In one embodiment, and as shown in FIGS. 1-4, at the second surface 23, the absorbent body 20 may include a backing 26. The backing 26 serves to limit fluid flow out of the absorbent core 25 at the second surface 23. The backing 26 can be a single layer or multilayer material of film or fabric, such as a woven, knitted, or nonwoven, or combinations of films, fabrics, or film and fabric.

Instead of, or in addition to an absorbent body 20 including a backing 26 at the second surface 23, the absorbent body 20 may comprise an absorbent core 25 contained within a pouch. The pouch could be a film, perforated film, or fabric, such as a woven, knitted, or nonwoven forming a pillow with the absorbent core 25 contained therein.

In one embodiment, and as shown in FIGS. 1-4, at the skin-facing surface, the absorbent body 20 may include a skin-facing contact layer 28. The skin-facing contact layer 28 can be is a soft, elastomeric adhesive that is gentle on fragile skin or a non-adherent film, net, fabric, non-woven that may be perforated or porous. The non-adherent perforated film, net, fabric, or nonwoven may have an adhesive on one or both sides. If the skin-facing contact layer 28 is an adhesive, it is typically discontinuously applied to the skin-facing surface 22 of the absorbent core 25 to enable more wound fluid to pass from the wound and into the absorbent core 25.

The first tape strip 30 comprises a substrate 32 coated with a soft, elastomeric adhesive 34. A first portion 35 of the first tape strip 30 is removably secured to the absorbent body 20.

In the embodiment shown in FIGS. 1-3, the first portion 35 of the first tape strip 30 is removably secured to the backing 26 at the second surface 23 of the absorbent body 20. A second portion 36 of the first tape strip 30 is removably secured to a tape release layer 37 to form a tab 38. In the embodiment shown in FIGS. 1-3, the second portion 36, and associated tab 38, extends outward from the perimeter 24 of the absorbent body 20.

Optionally, one or more additional tape strips may be included. As shown in FIGS. 1-3, a second tape strip 40 is included. The second tape strip 40 comprises a substrate 42 coated with a soft, elastomeric adhesive 44. A first portion 45 of the second tape strip 40 is removably secured to the absorbent body 20. In the embodiment shown in FIGS. 1-3, the first portion 45 of the second tape strip 40 is removably secured to the backing 26 at the second surface 23 of the absorbent body 20. A second portion 46 of the second tape strip 40 is removably secured to a tape release layer 47 to form a tab 48. In the embodiment shown in FIGS. 1-3, the second portion 46, and associated tab 48, extends outward from the perimeter 24 of the absorbent body 20.

Optionally, the tape strips 30, 40 can have one or more slits 90 cut into it, which would facilitate tearing of the tape strips 30, 40 along the side of the absorbent core to help create additional tape strips 30, 40 for other securement needs. There could be more than one slit in the tape strips 30, 40. The slit 90 may be longitudinally aligned to the tape strip 30, 40, laterally aligned to the tape strip 30, 40, or may be at an angle to the tape strip 30, 40, see FIG. 2.

Because the tape strips include a removable or repositionable adhesive, any number of additional tape strips may be included, where the tape strips may be partially or entirely secured to the absorbent body 20 or other portion of the wound dressing assembly 10. For example, FIG. 3 shows an additional tape strip 60 that is releasably secured to one side of the tape release layer 47. It is understood that similar to the first tape strip 30, any additional tape strip may be partially secured to the absorbent body 20 by inclusion of a release liner adhered to a portion of the tape strip to form a tab.

In the embodiment shown in FIGS. 1-3, the tape release layer 37 on the second portion 36 of the first tape strip 30 also partially covers the skin-facing surface 22 of the absorbent body 20. Also, the tape release layer 47 on the second portion 36 of the second tape strip 40 also partially covers the skin-facing surface 22 of the absorbent body 20. It is understood that each second portion 36, 46 may include a tape release layer 37, 47 and the skin-facing surface 22 may include a separate release liner.

To use the wound dressing assembly 10, the outward extending tab 38, 48 are useful for holding and positioning the absorbent body 20 over the skin 12 during application and also for pulling the tape strip from the absorbent body 20. During application to skin 12, the tape release layer 37, 47 (see FIG. 3) are removed. The wound dressing assembly 10 is positioned over a wound on skin 12. The tape strips 30, 40 secure the absorbent body 20 to the skin 12. The tape strips 30, 40 are attached to the absorbent body 20 securely enough to be able to hold the absorbent body 20 to skin 12. The tape strips 30, 40 are easily removable from the skin 12 and the absorbent body 20 if it is desired to have the strips removed. For example, FIG. 4 shows the wound dressing assembly 10 with the absorbent body 20 secured to the skin 12 by the second tape strip 40. The first tape strip 30 has been removed. It is understood that the first tape strip 30 could be removed before or after securement to the skin 12. In addition, it is understood that the strips may be removed from the absorbent body 20 without damaging, distorting or tearing any portion of the absorbent body 20 including the backing 26, if included.

The removed first tape strip 30 remains tacky for additional securement needs. For example, the removed first tape strip 30 could be used to secure a medical devices or tubing.

The adhered second tape strip 40 could remain in contact with the skin 12 for holding the absorbent body 20 to the skin. Furthermore, it is understood that both the first and second tape strips and any additional tape strips could remain secured to the absorbent body 20 for holding the absorbent body 20 to the skin 12. Alternatively, even the second tape strip 40, shown in FIG. 4, could be removed from the absorbent body 20 while the absorbent body 20 remains in contact with the wound on the skin 12. An additional securing mechanism, which would not have adhesive directly on the skin, such as a compression bandage could be applied to hold the absorbent body 20 to the skin 12.

As mentioned above, tape strips 30 and 40 could be used to secure the absorbent body 20 to the skin. Tape strip 60 and another tape strip, if included, could then be removed from the tape release layer and used to secure the absorbent body 20 to the skin along edges that tape strip 30 and 40 do not cover. Thereby creating an adhesive border that surrounds the absorbent body 20 for securement to skin 12.

Figure 5:
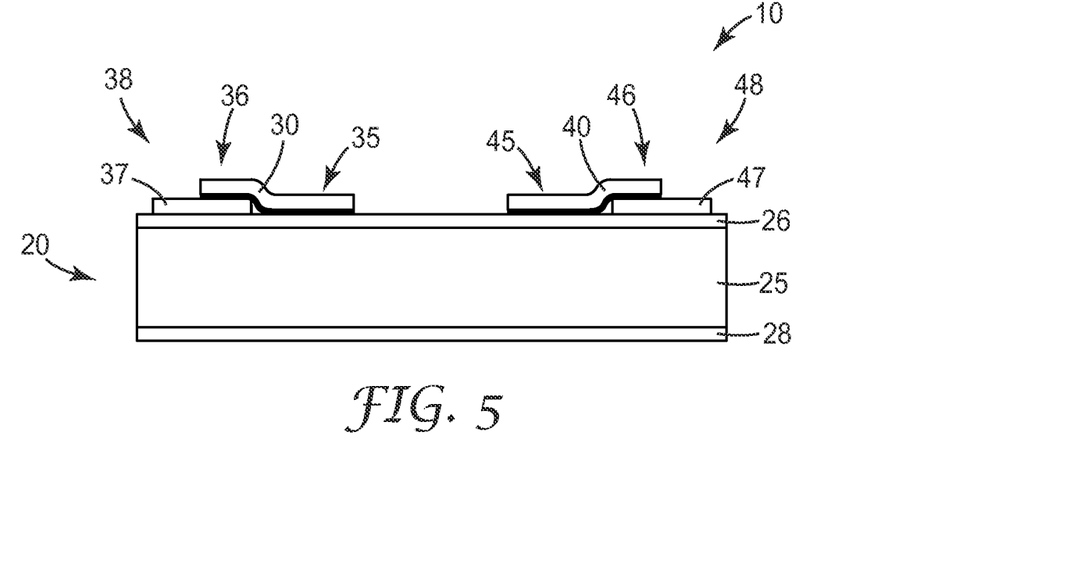
FIG. 5 is a side view of another embodiment of a wound dressing assembly.

FIG. 5 is a side view of another embodiment of a wound dressing assembly 10. The wound dressing assembly 10 comprises an absorbent body 20 and a first tape strip 30 and a second tape strip 40. The absorbent body 20 includes a first skin-facing surface 22 and a second surface 23, opposite the skin-facing surface surrounded by a perimeter 24. The absorbent body 20 includes an absorbent core 25. As shown in this embodiment, the absorbent body 20 includes a backing 26 at the second surface 23 of the absorbent core 25. As shown in this embodiment, at the skin-facing surface, the absorbent body 20 includes a skin-facing contact layer 28. A release liner (not shown) may cover the skin-facing contact layer 28, especially if the skin contact layer is an adhesive.

A first portion 35 of the first tape strip 30 is removably secured to the absorbent body 20. In the embodiment shown in FIG. 5, the first portion 35 of the first tape strip 30 is removably secured to the backing 26 at the second surface 23 of the absorbent body 20. A second portion 36 of the first tape strip 30 is removably secured to a tape release layer. Tape release layer 37 is separate and not adhered to the backing 26 such that a tab 38 is formed on the tape strip 30.

A first portion 45 of the second tape strip 40 is removably secured to the absorbent body 20. In the embodiment shown in FIG. 5, the first portion 45 of the second tape strip 40 is removably secured to the backing 26 at the second surface 23 of the absorbent body 20. A second portion 46 of the second tape strip 40 is removably secured to a tape release layer 47. Tape release layer 47 is separate and not adhered to the backing 26 such that a tab 48 is formed on the second tape strip 40.

To use the wound dressing assembly 10, the absorbent body 20 is positioned over the skin 12. The tape strips 30, 40 can be removed from the absorbent body 20. The tabs 38, 48 make the tape strip 30, 40 readily able to be removed. Once removed, the tape release layers 37, 47 are removed from the tape strips 30, 40. The removed tape strips 30, 40 could be used for a number of purposes such as securing the absorbent body 20 to the skin 12 or for securing a medical devices or tubing.

Figure 6:
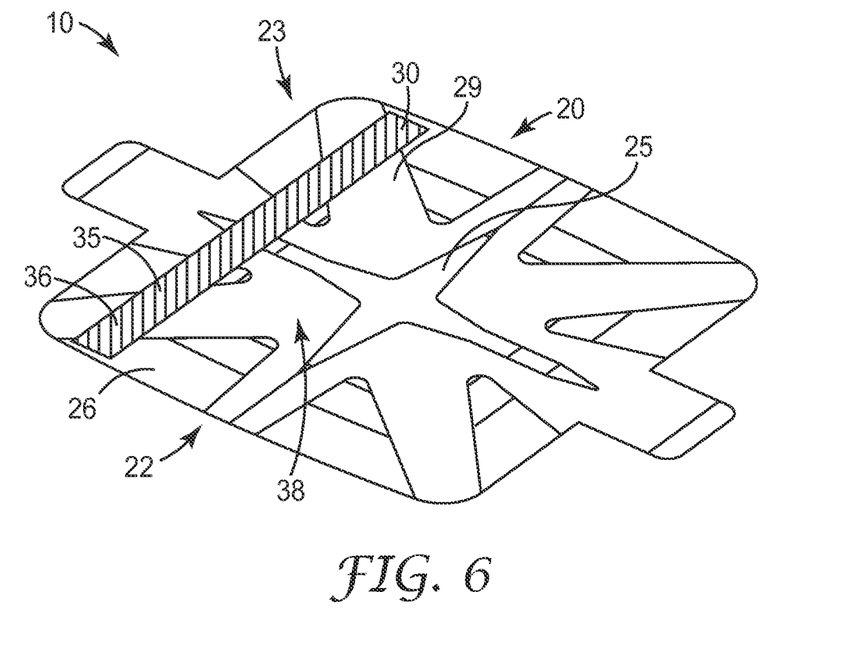
FIG. 6 is a perspective view of another embodiment of a wound dressing assembly.

FIG. 6 is a perspective view of another embodiment of a wound dressing assembly 10. The wound dressing assembly 10 in FIG. 6 is similar to the embodiment shown in FIG. 5, except that for the absorbent body 20 in the embodiment shown in FIG. 6 the backing 26 extends beyond all edges of the absorbent core 25 creating a bordered or island dressing and a single tape strip 30 is included. A carrier 29, as described in U.S. patent publication 2004/0162512 (Liedtke, et. al.) and similarly shown in U.S. Designs 511,005 and 493230, the disclosure of which are herein incorporated by reference, can be attached to the backing 26 to provide structural support to the thin film backing 26 prior to application to the skin 12.

A first portion 35 of the first tape strip 30 is removeably secured to the absorbent body 20 and in particular to the backing 26 at the second surface 23 of the absorbent body 20. A second portion 36 of the first tape strip 30 is removably secured to a tape release layer 37, which in this embodiment is the carrier 29. Carrier 29 is separate and removably from the backing 26 such that a tab 38 is formed on the tape strip 30 attached to the carrier 29. It is understood that the tape strip 30 could be any length and may extend from completely from end to end of the absorbent body 20.

To use the wound dressing assembly 10, the absorbent body 20 is positioned over the skin 12. Prior to applying to skin 12, the release liner (not shown) is removed from the skin-facing surface 22 of the absorbent body 20. After application to the skin, removal of the carrier 29 from the absorbent body 20 also lifts the tape strip 30. Then, the lifted tape strip 30 can be easily removed from the carrier 29. The removed tape strip 30 could be used for a number of purposes such as securing the absorbent body 20 to the skin 12 or for securing a medical devices or tubing.

Absorbent Core

The absorbent body include an absorbent core. The absorbent core may comprise any material that is conformable, non-irritating to the wearer's skin, and capable of absorbing and retaining liquids. The absorbent core may be a single layer or multilayer material, wherein if it is a multilayer material each layer may be of the same material or of different materials.

Examples of materials that would be suitable for the absorbent core include creped cellulose wadding; melt blown polymers; chemically stiffened, modified or cross-linked cellulosic fibers; tissue; absorbent foams; absorbent sponges; superabsorbent polymers; absorbent gelling materials; or any other known absorbent material or combinations of materials. The absorbent core may further comprise minor amounts (typically less than 10%) of non-liquid absorbent materials, such as adhesives, waxes, oils, antimicrobials, active ointments, and the like, for example.

In one embodiment the absorbent core is an open-cell foam. The foam may include a synthetic polymer that is adapted to form a conformable open-cell foam that absorbs the wound exudate. Examples of suitable materials for the foams include synthetic organic polymers including, but not limited to: polyurethanes, carboxylated butadiene-styrene rubbers, polyesters, and polyacrylates. The polymeric foams can be made of one or more types of monomers (e.g., copolymers) or mixtures (e.g., blends) of polymers. Examples of foam materials are described in the book entitled "Flexible Polyurethane Foams", Dow Polyurethanes, editors R. Herrington and K. Hock, 1997.

The foams can be of a wide range of thicknesses; from about 0.5 mm or 1 mm to about 30 mm or 80 mm thick. Furthermore, they can include one or more layers tailored to have the desired properties. These layers can be directly bonded to each other or bonded together with adhesive layers. Optionally, disposed between these layers can be one or more layers of polymeric netting or nonwoven, woven, or knit webs for enhancing the physical integrity of the foam.

In one embodiment, the second surface of the absorbent core 25 comprises a foam with a skin to prevent fluid passage through the absorbent core 25. In such an embodiment, a backing 26 may not be necessary.

In another embodiment, the absorbent core comprises superabsorbing particles or fibers contained within a porous pouch. Examples include superabsorbent fiberous webs that are available from National Nonwovens, Cincinnati, Ohio or sachets containing superabsorbent material such as Sorbion Sachet S available from Sorbion AG, Senden, Germany.

Optionally the absorbent body can include a wound-contacting layer bonded to the skin-facing surface of the absorbent body. Examples of such wound-contacting layers include polymeric netting and porous (e.g., perforated) films, or other conventional materials that prevent the dressing from sticking to the wound. This wound-contacting layer can be bonded directly bonded to the absorbent core (e.g., cast or thermomechanical bonding), or bonded to the absorbent core using an adhesive layer, for example.

One example of a suitable absorbent core is found in a 3M Tegaderm™ High Performance Foam Dressing available from 3M Company of St. Paul, Minn. Suitable constructions for the absorbent core are disclosed in U.S. Pat. Nos. 6,838,589; 7,030,288; and 7,612,248, the disclosure of which are herein incorporated by reference.

Backing

The absorbent body may include a backing 26 at the second surface, opposite the skin facing surface. The backing is bonded to the surface of the absorbent core opposite the skin-facing surface. The backing typically includes a liquid-impervious, moisture-vapor permeable polymeric film, although it can include a variety of other materials, which are preferably used in combination with a liquid-impervious, moisture-vapor permeable polymeric film. The liquid-impervious, moisture-vapor permeable polymeric film is a conformable organic polymeric material that preferably retains its structural integrity in a moist environment. Herein, "conformable" films are those that conform to a surface, even upon movement of the surface, as with the surface of a body part. Suitable films have a composition and thickness that allow for the passage of moisture vapor through them. The film aids in the regulation of water vapor loss from the wound area beneath the dressing. The film also acts as a barrier to both bacteria and to liquid water or other liquids.

The moisture-vapor permeable polymeric films can be of a wide range of thicknesses. Preferably, they are from about 10 microns or 12 microns to 75 microns or 250 microns thick. Furthermore, they can include one or more layers tailored to have the desired properties. These layers can be coextruded and/or bonded together with adhesive layers, for example, as long as the overall properties of the film and article, as described herein, are met.

Examples of suitable materials for the liquid-impervious, moisture-vapor permeable polymeric films include synthetic organic polymers including, but not limited to: polyurethanes commercially available from B.F. Goodrich, Cleveland, Ohio, under the trade designation ESTANE, including ESTANE 58237 and ESTANE 58245; poly-amide block copolymers commercially available from Elf Atochem, Philadelphia, Pa., under the trade designation PEBAX, including PEBAX MV 1074; poly-ester block copolymers commercially available from DuPont, Wilmington, Del., under the trade designation HYTREL. The polymeric films can be made of one or more types of monomers (e.g., copolymers) or mixtures (e.g., blends) of polymers. An example material is thermoplastic polymers (e.g., those that soften when exposed to heat and return to their original condition when cooled), such as thermoplastic polyurethane.

Backings of the wound dressing assemblies of the present invention can be other breathable materials including, for example, nonwoven, woven, and knit webs, porous films (e.g., provided by perforations or microporous structure), or other known backings. One such nonwoven web is a melt processed polyurethane (such as that available under the trade designation MORTHANE PS-440 from Morton International, Seabrook, N.H.), or hydroentangled nonwoven polyester or rayon-polyester webs (such as those available under the trade designation SONTARA 8010 or SONTARA 8411 from DuPont, Wilmington, Del.). Other suitable breathable backings are apertured films such as DELNET from DeltStar Technologies (Middletown, Del.).

Backings may be a combination of a liquid-impervious, moisture-vapor permeable polymeric film and a moisture-vapor permeable nonwoven, woven, or knit web, or a porous film that can, among other advantages, impart enhanced structural integrity and improved aesthetics to the dressings. The layers within the backing are preferably bonded together using an adhesive layer, for example, that can be continuous or discontinuous (e.g., such as that produced with a pattern-coated adhesive layer), although other means of bonding can be used including thermomechanical bonding, such as thermal bonding or ultrasonic welding.

The backing may have irregularities (e.g., non-wovens, wrinkled film backing, embossed film pattern) in its structure which can facilitate removal of the tape strips from the backing because of a decrease in the contact surface area between the tape and the backing.

Adhesive

Tape strip 30, 40 is coated with a soft, elastomeric adhesive that is gentle on the skin. If included, the adhesive at the skin-facing surface 22 of the absorbent body 20 can be a soft, elastomeric adhesive. Silicone adhesives are soft, elastomeric adhesives that can be used on the tape strip to provide removable securement to the absorbent body. Generally, silicone adhesives can provide suitable adhesion to skin while gently removing from skin. Suitable silicone adhesives are disclosed in PCT Publications WO2010/056541 and WO2010/056543, the disclosure of which are herein incorporate by reference. Other suitable silicone adhesive elastomers are disclosed in U.S. Pat. No. 6,479,724, the disclosure of which is herein incorporated by reference. Polyurethanes can also be a soft, elastomeric adhesive that can provide removable securement to the absorbent body while providing adhesion to skin and gentle removing from skin.

The backing may be coextensive with the absorbent core (such as FIG. 5) and may be secured to the core with an adhesive. In other embodiments the backing may have a greater surface area than the surface area of the absorbent core (such as FIG. 6) and the area of the backing contacting the skin may be coated with an adhesive. For these applications, the adhesive typically is a pressure sensitive adhesive, and particularly adhesives that can be applied to skin such as the acrylate copolymers described in U.S. Pat. No. RE 24,906, the disclosure of which is hereby incorporated by reference, particularly a 97:3 iso-octyl acrylate: acrylamide copolymer. Another adhesive is an 70:15:15 isooctyl acrylate: ethyleneoxide acrylate:acrylic acid terpolymer, as described in U.S. Pat. No. 4,737,410 (Example 31), the disclosure of which is hereby incorporated by reference. Other useful adhesives are described in U.S. Pat. Nos. 3,389,827, 4,112,213, 4,310,509, and 4,323,557, the disclosures of which are hereby incorporated by reference. Inclusion of medicaments or antimicrobial agents in the adhesive is also contemplated, as described in U.S. Pat. Nos. 4,310, 509 and 4,323,557 both of which are hereby incorporated by reference. Silicone adhesive can also be used. For this application, typically the adhesive is able to transmit moisture vapor at a rate greater to or equal to that of human skin. While such a characteristic can be achieved through the selection of an appropriate adhesive, it is also contemplated in the present invention that other methods of achieving a high relative rate of moisture vapor transmission may be used, such as pattern coating the adhesive on the backing, as described in U.S. Pat. No. 4,595,001 and U.S. Pat. App. Pub. 2008-0233348, the disclosures of which are herein incorporated by reference.

Tape Strip

The adhesive tape strips used in the present invention contain a soft, elastomeric adhesive that provides removable securement to the absorbent body, adhesion to skin, and gentle removing from skin. The soft, elastomeric adhesive may be silicone or polyurethane. The adhesive should be appropriate for contact with human or animal surfaces to provide closure for wound sites, additional securement to the absorbent core, or to secure other medical articles such as catheter tubes. The substrate for use as the tape strip can be any number of substrates including paper, film, woven, knitted, or nonwoven material, or combinations thereof. One example of a suitable tape strip is a strip of 3M Kind Removal Silicone Tape available from 3M Company of St. Paul, Minn.

Optional Tape Release Layer

A tape release layer may be used to cover a portion of the soft adhesive on the tape strip. The tape release layer can be made of polyethylene, polypropylene, kraft papers, polyester or composites of any of these materials. In one embodiment, the tape release layer is an embossed polyethylene or polypropylene material. An example of an embossed polyethylene liner is High Density Polyethylene with embossing design 124 from Huhtamaki (Forchheim, Germany).

In one embodiment, the side of the embossed liner without the protrusions that extend out to a point or island is in contact with the soft adhesive of the tape strip that is also releasably attached to the backing. An optional tape strip (for further secural of tubes or the absorbent dressing) can then be attached to the embossed liner on the side with the protrusions. Attaching the optional tape strip to the side of the embossed liner with protrusions results in easier removal of the optional tape strip from the liner.

In another embodiment, the tape release layer is coated with release agents such as fluorochemicals or silicones. For example, U.S. Pat. No. 4,472,480, the disclosure of which is hereby incorporated by reference, describes low surface energy perfluorochemical liners. In one embodiment, the liners are papers, polyolefin films, or polyester films coated with silicone release materials. Examples of commercially available silicone coated release papers are supplied by Wausau Paper Specialty Products (Rhinelander, Wis.) and Mondi Packaging (Lancaster, Ohio). One suitable release liner is a 60# per 3000 square feet bleached kraft SC RLSE D11 442-6001 paper liner available from Wausau Paper Specialty Products. Optionally, the tape release layer also functions as a tab which facilitates the easy removal of the tape strip from the backing of the dressing.

Surprisingly, for the embodiments shown in FIGS. 5 and 6, it is possible to remove the tape strip from the backing by gasping the tab of the tape release layer and pulling the tape strip off the backing even if the peel force to remove the tape from the backing is greater than the peel force to remove the tape release layer from the tape strip.

Optional Release Liner

A release liner may be used to cover any exposed adhesive on the absorbent core or backing. Release liners can be made of kraft papers, polyethylene, polypropylene, polyester or composites of any of these materials. In one embodiment, the liners are coated with release agents such as fluorochemicals or silicones. For example, U.S. Pat. No. 4,472, 480, the disclosure of which is hereby incorporated by reference, describes low surface energy perfluorochemical liners. In one embodiment, the liners are papers, polyolefin films, or polyester films coated with silicone release materials. Examples of commercially available silicone coated release papers are supplied by Wausau Paper Specialty Products (Rhinelander, Wis.) and Mondi Packaging (Lancaster, Ohio). One suitable release liner is a 60# per 3000 square feet bleached kraft SC RLSE D11 442-6001 paper liner available from Wausau Paper Specialty Products. Optionally, the release liner for the tape strip also functions as a tab which facilitates the easy removal of the tape strip from the backing of the dressing.

Although specific embodiments of this invention have been shown and described herein, it is understood that these embodiments are merely illustrative of the many possible specific arrangements that can be devised in application of the principles of the invention. Numerous and varied other arrangements can be devised in accordance with these principles by those of ordinary skill in the art without departing from the spirit and scope of the invention. Thus, the scope of the present invention should not be limited to the structures described in this application, but only by the structures described by the language of the claims and the equivalents of those structures.

What is claimed is:

1. A wound dressing assembly comprising:
an absorbent body comprising a first skin-facing surface and a second surface, opposite the first surface, and a perimeter including first and second opposing edges of the absorbent body when viewed from above;
a first tape strip comprising a substrate coated with a soft, elastomeric adhesive;
wherein a first portion of the first tape strip is removably secured directly to the second surface of the absorbent body;
wherein a second portion of the first tape strip extends beyond the perimeter of the absorbent body and is removably secured directly to a first tape release layer to form a tab;
wherein a portion of the first tape release layer covers at least a portion of the first skin-facing surface of the absorbent body;
a second tape strip comprising a substrate coated with a soft, elastomeric adhesive;

wherein a first portion of the second tape strip is removably secured directly to the second surface of the absorbent body;

wherein a second portion of the second tape strip extends beyond the perimeter of the absorbent body and is removably secured directly to a second tape release layer to form a tab;

wherein a portion of the second tape release layer covers at least a portion of the first skin-facing surface of the absorbent body;

wherein the first portion of the first tape strip that is removably secured directly to the second surface of the absorbent body covers a portion of the first opposing edge of the absorbent body;

wherein the first portion of the second tape strip that is removably secured directly to the second surface of the absorbent body covers a portion of the second opposing edge of the absorbent body;

wherein the first portion of the first tape strip is spaced apart from the first portion of the second tape strip.

2. The wound dressing assembly of claim 1, wherein the adhesive on the tape strip is a silicone adhesive.

3. The wound dressing assembly of claim 1, wherein the absorbent body comprises an absorbent core and a film backing.

4. The wound dressing assembly of claim 1, wherein the absorbent body comprises an absorbent core contained within a pouch.

5. The wound dressing assembly of claim 4, wherein the absorbent core comprises a foam, nonwoven, woven, knitted, superabsorbent or combinations of one or more thereof.

6. The wound dressing assembly of claim 1, further comprising a skin-contact adhesive on the skin-facing surface of the absorbent body.

7. The wound dressing assembly of claim 6, further comprising a second release liner covering at least the skin-facing surface of the absorbent body.

* * * * *

UNITED STATES PATENT AND TRADEMARK OFFICE
CERTIFICATE OF CORRECTION

PATENT NO.        : 9,452,087 B2
APPLICATION NO.   : 14/131568
DATED             : September 27, 2016
INVENTOR(S)       : David Holm et al.

It is certified that error appears in the above-identified patent and that said Letters Patent is hereby corrected as shown below:

In the Specification

<u>Column 8</u>
Line 21, delete "DeltStar" and insert -- DelStar --, therefor.

Signed and Sealed this
Seventh Day of November, 2017

Joseph Matal
*Performing the Functions and Duties of the
Under Secretary of Commerce for Intellectual Property and
Director of the United States Patent and Trademark Office*